United States Patent [19]

Jampel et al.

[11] Patent Number: 4,844,093
[45] Date of Patent: Jul. 4, 1989

[54] TOOL FOR FOLDING AND INSERTING INTRAOCULAR LENSES

[75] Inventors: Robert S. Jampel, Bloomfield Hills; Dian X. Shi, Detroit, both of Mich.

[73] Assignee: Kresge Eye Institute, Detroit, Mich.

[21] Appl. No.: 126,900

[22] Filed: Nov. 30, 1987

[51] Int. Cl.⁴ .............................................. A61B 17/28
[52] U.S. Cl. ................................................. 128/303 R
[58] Field of Search ..................... 128/303 R, 321, 354

[56] References Cited

U.S. PATENT DOCUMENTS

| | | | |
|---|---|---|---|
| 4,170,043 | 10/1979 | Knight et al. | 128/303 R X |
| 4,198,980 | 4/1980 | Clark | 128/303 R |
| 4,573,998 | 3/1986 | Mazzocco | 128/321 X |
| 4,747,404 | 5/1988 | Jampel et al. | 128/303 R |
| 4,759,359 | 7/1988 | Willis et al. | 128/303 R |

*Primary Examiner*—Dalton L. Truluck
*Attorney, Agent, or Firm*—Harness, Dickey & Pierce

[57] ABSTRACT

An intraocular lens folding and inserting tool is formed of a folding clamp which bends the lens in half between spaced apart, resilient forceps tips which are temporarily secured within the folding clamp. The forceps is separated from the folding clamp for holding the folded lens and for inserting the folded lens into the anterior chamber of an eye through a small incision in the limbus of the eye. The folding clamp includes a U-shaped channel having side walls, a base and an open side, within which channel a lens is positioned. The forceps tips are secured in the channel between the side walls and between the lens and the channel base. A clamp pressure member engages and presses the center line of the lens towards the channel base for folding the lens in half between the tips. The forceps tips, which are made of axially elongated, resilient wire loops, are moved towards each other for resiliently holding the folded lens and for inserting the folded lens through the incision into the chamber where the folded lens is released.

15 Claims, 1 Drawing Sheet

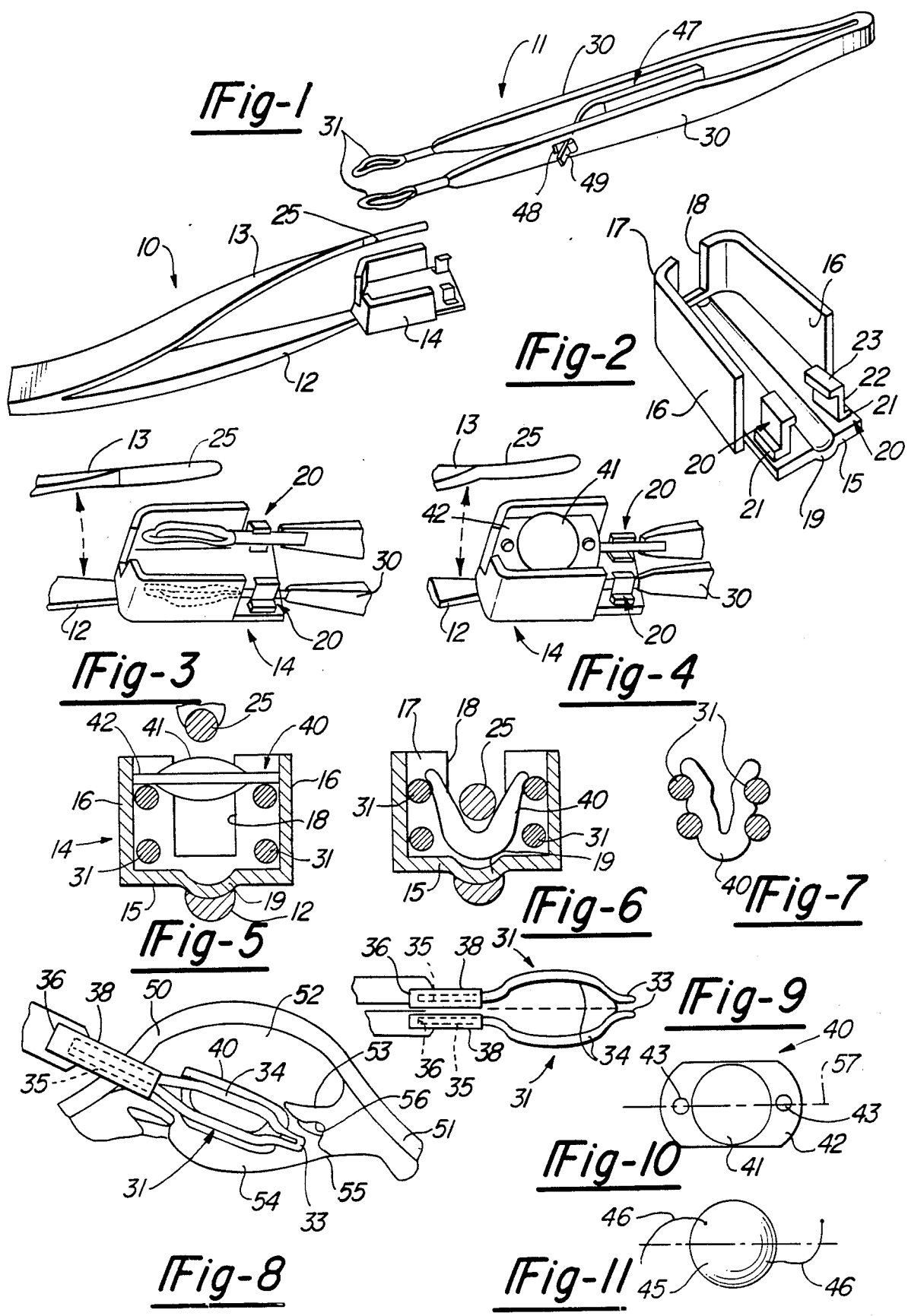

4,844,093

TOOL FOR FOLDING AND INSERTING INTRAOCULAR LENSES

This invention relates to a forceps type of surgical tool for folding a synthetic, intraocular lens and for inserting the folded lens into the anterior chamber of an eye through a small incision in the limbus.

A surgical operation for removal of a defective natural lens and replacement of a synthetic lens, generally involves making an incision in the limbus or margin of the cornea of the eye. The natural lens is surgically removed through the incision by emulsifying it with an ultrasonic probe and then sucking it out. Then the synthetic lens is inserted through the incision into the anterior chamber of the eye where it is positioned to replace the natural lens. After the synthetic lens is properly positioned, the incision is closed with sutures and is allowed to heal.

In the past, synthetic replacement lenses were made of a synthetic rigid material that was sized and shaped to fit within the anterior chamber of the eye in place of the natural lens. A substantial size incision was required, such as on the order of roughly 12 millimeters, for inserting the rigid lens into the anterior chamber, beneath the cornea.

Recently, resiliently flexible or foldable synthetic plastic lenses have been developed. These may be used instead of using rigid lenses. Because the foldable or flexible synthetic lenses may be rolled or folded, they may be inserted into the anterior chamber through a considerably smaller incision than that which was previously required for insertion of the rigid lens. For example, an incision of roughly 3.5–4 millimeters may be adequate for insertion of a rolled or folded lens. After the folded lens is inserted through the smaller incision into the anterior chamber for subsequent positioning into the sulcus or capsule, the lens resiliently returns to its normal, unfolded shape.

The ability to insert the lens in folded condition and to rely upon its returning to its unfolded condition, has been a substantial advantage in reducing the length of the incision which was previously required for this type of eye surgery. As is known, the smaller the incision, the less the induced astigmatism caused by the operation, the faster the wound heals, the less bleeding occurs and the less intraocular inflammation occurs. A smaller incision requires a lesser number of sutures to the point where only one or two suture may be adequate for closing the wound. Consequently, there is a considerable advantage in using a foldable lens, insertable through a smaller incision, in place of earlier, rigid synthetic lenses.

But, foldable lenses are easily damaged in the course of folding them and in handling them. In addition, they may cause damage to the eye tissues during the insertion operation. Particularly, the marginal edges of the foldable lenses, which are more delicate or thinner than the main body portion of the lenses, are especially easily damaged. Therefore, it is necessary to fold a lens, hold it in folded condition, and insert it through the eye incision into the anterior chamber by tools or techniques which minimize or eliminate damaging or scratching either the lens or the eye tissues. Thus, this invention relates to a surgical tool, of a forceps type, which facilitates folding the lens in half and inserting the folded lens through a small incision into the eye chamber without damaging the lens or the eye tissue.

SUMMARY OF INVENTION

This invention contemplates a surgical tool which essentially is formed of two forceps-like instruments which are releasably interlocked for folding and gripping the folded lens, but are separated so that one may be used for insertion of the folded lens within the eye chamber. One of the instruments forms a folding clamp within which the lens is folded, and the other forms a lens gripping and insertion tool. The folding action is performed by, first, temporarily holding the tips of the gripping instrument legs within an elongated open channel formed on one of the legs of the folding instrument. Second, an unfolded lens is positioned within the elongated, open channel and upon the spaced apart leg tips of the holding instrument. Third, the opposite leg of the folding clamp instrument presses the middle of the unfolded lens more deeply into the channel between the leg tips of the gripping instrument, for folding the lens between the tips.

Thereafter, the tip of the forceps-like legs of the gripping instrument are disconnected from the channel with the folded lens tightly gripped between the tips. Then, the gripping instrument tips, containing the folded lens, is inserted through the limbus incision into the eye interior where the folded lens is released. The resilient lens unfolds itself within the anterior chamber after it is released.

The invention further contemplates forming the gripping and insertion instrument with springy or resilient tips that are formed of elongated loops made of wire bent into a U-shape. These tips are shaped to resiliently grip the opposite sides of the folded lens, but to resiliently yield, as necessary, to avoid breaking or otherwise damaging the folded lens. Also, these tips are shaped to facilitate their entry through the eye incision into the anterior chamber.

An object of this invention is to provide a relatively inexpensive, easily operated tool for folding the lens in half, for gripping the folded lens, for maintaining the lens in folded condition until it is inserted within the eye, and for inserting the lens into the interior of the eye through a small incision.

Another object of this invention is to provide an instrument which folds and grips the lens between resilient gripping tips of a forceps type device which protects against damage to the lens, particularly its thinner marginal portions and minimizes damage to the eye tissues.

Further objects and advantages of this invention will become apparent upon reading the attached description, of which the attached drawings form a part.

DESCRIPTION OF DRAWINGS

FIG. 1 is a perspective view of the two forcep-like instruments shown separately, but with the resilient tips of one in alignment with the channel of the other.

FIG. 2 is an enlarged, perspective view of the clamping channel.

FIG. 3 is a perspective view showing the resilient tips of the gripping instrument arranged within the channel of the clamping instrument.

FIG. 4 is a perspective view, similar to FIG. 3, showing an unfolded lens positioned within the clamping channel upon the resilient tips of the gripping instrument.

FIG. 5 is an enlarged, cross-sectional view showing an unfolded lens arranged within the clamping channel upon the resilient tips of the gripping instrument.

FIG. 6 is a cross-sectional view, similar to FIG. 5, but showing the lens folded into the channel.

FIG. 7 is a cross-sectional, fragmentary view of the folded lens gripped between the tips of the gripping instrument.

FIG. 8 is an enlarged, schematic view of the gripping instrument inserted within the anterior chamber of an eye for positioning a folded lens within the chamber.

FIG. 9 is a plan view of the opposed resilient tips of the gripping instrument.

FIG. 10 is a plan view of one type of foldable lens, and

FIG. 11 is a plan view of another type of foldable lens.

DETAILED DESCRIPTION

FIG. 1 illustrates the forcep-like clamping instrument 10 and gripping and insertion instrument 11 which are used together and separately for folding and inserting a synthetic plastic lens within an eye cavity. The clamping instrument 10 is formed with a lower leg 12 and an upper leg 13 which are fastened together at one of their ends so that their opposite ends may be squeezed toward each other and resiliently spring apart.

A clamping channel 14 (see FIG. 2) is fixed upon the free end of the lower leg 12, as for example by soldering the channel to the leg. The channel includes a base 15 and opposing side wall 16 which are of a lesser length than the base. The rear of the channel is closed by a rear wall 17, which may be curved for accommodating to the curvature of a lens, as will be described below. A slot 18 is formed in the rear wall and a groove is bent along the longitudinal axis of the base 19.

A pair of opposed clips 20 are secured upon the portion of the base 15 which extends beyond the side walls 16. These clips, which may be made of sheet metal, each have a lower end 21 which is fastened to the channel base 15 and upstanding side portions 22 which terminate in upper clip flanges 23.

The upper leg 13 of the clamping instrument 10 has its free end formed as an elongated rod-like pressure member 25. The pressure member may be manually squeezed into the channel, in longitudinal alignment with the axis of the channel, towards the channel base. Release of the manual squeezing force results in the upper leg, with the pressure member end 25, resiliently springing out of and above the open upper portion of the channel.

The gripping and insertion forcep-like instrument 11 is provided with a pair of opposed legs 30 which are connected together at one end for squeezing the legs together and permitting them to resiliently spring apart. The free end of each of the legs 30 is provided with an elongated spring tip 31. The tips are made of resilient wire loops, with the wire bent into elongated U-shapes. The wires at the bight or lead end portion are arranged closely together to form a lead end or entry end 33. An intermediate portion 34 is provided where the wires are spaced apart and the free end portions 35 of the wire are bent closely adjacent.

The springy wire tips which may be made of a stainless steel that is relatively springy or the like material, are mounted in edge sockets 36 formed in the ends of the legs 30. A sleeve 38 surrounds the free end portions of the wire loops and is fastened, as by welding or soldering or the like in the sockets 36.

As can be seen in the plan view of FIG. 9, the intermediate portions of the wire loops are bowed apart a small amount. For illustration purposes, the bows are exaggerated in FIG. 9. The lead end or entry ends 33 are closer together and may touch when the legs 30 are squeezed together.

Foldable, synthetic plastic lenses essentially come in two forms. One form of lens 40 has a bulged center 41 and a surrounding thin, edge border 42, which in the illustration of FIG. 7 is shown as being roughly rectangular in shape. The opposite edges of the border are curved slightly. Holes 43 are formed in the opposite ends of the border to enable the surgeon to fasten the lens in place within the posterior chamber of the eye.

An alternative form of lens is shaped as a circular, centrally bulged disk 45. Typically, this form comes with springy plastic wires 46 secured to its opposite edges to enable fastening it in place. The specific form of lens may change somewhat, but it is contemplated that the tool of this invention will handle these various shapes.

In operation, the springy tips 31 of the gripping instrument 11 are positioned within the clamping channel 14 and held in the channel by the clips 20 which engage over the upper edges of the tips (see FIG. 3). Next, an unfolded lens 40 (or disk type lens 45) is placed within the channel, between the side wall 16 and rested upon the upper edges of the tips 31 (see FIG. 4). As shown in the cross-sectional view in FIG. 5, the elongated pressure member end 25 of the upper leg 13 is centered, relative to the channel, above the unfolded lens. By squeezing the upper leg 13 towards the lower leg 12, the pressure member moves downwardly, through the slot 18 in the channel rear wall 17, to engage the center of the lens, along a center line 57. Squeezing the pressure member 25 against the lens causes the central portion of the lens to bend downwardly, towards the base of the channel, for folding the lens in half, as schematically shown in FIG. 6. The folded lens is pushed downwardly between the opposed spring tips 31 of the two legs of the gripping instrument.

Next, the two legs 30 of the gripping instrument 11 are squeezed together to complete the folding of the lens in half, as shown in FIG. 7. At that point, the legs may be held in locked position by means of a releasable latch (see FIG. 1). The latch may comprise an elongated strip of springy metal 47 fastened to one of the legs 30. The springy tongue-like free end of the strip extends through a hole 48 in the opposite leg and the tongue temporarily latches against the edge of the hole by means of suitable ridges or bumps 49 formed on the tongue. The tongue-like strip may be released by manually moving it away from the edge of the hole against which it is locked by the ridges.

Some time after the lens is bent in half and gripped between the springy tips 31 of the gripping instrument, the instrument is removed endwise from the channel 14 and is separately used for insertion of the lens into the anterior chamber of the eye. FIG. 8 schematically illustrates an eye and the insertion of the lens in the eye. The diagram of FIG. 8 schematically shows the eye cornea 50, the sclera 51 and the anterior chamber 52. The lead ends 33 of the tips 31 are inserted through a small incision, such as on the order of 3.5-4 mm, in the limbus or margin of the cornea and the tips are inserted into the anterior chamber 52. The iris 53 may be manipulated out of the way sufficiently so that the tips may position the folded lens at or in the capsule 54, from which the natural lens had been removed earlier.

As shown in the drawing, the capsule is supported by the suspensory ligament 55 above which is located the posterior chamber 56.

After the folded lens is appropriately positioned within the anterior chamber, the tips are sufficiently separated, by released the latch or by releasing the manual pressure if it is held by a manual squeeze. The instrument may then be removed endwise through the incision, leaving the folded lens to resiliently unfold. Thereafter, the surgeon can manipulate the lens in the appropriate location and fix it in place.

Significantly, the lens, whether of the border type or the disk type, is protected against damage by the resiliency of the wire tips. That is, the lens, when folded, is held along two pairs of opposing lines, each representing one of the wire lengths, which lines are separated and resilient. Thus, the yieldability of the tips, coupled with the resilient yieldability of the lenses, substantially reduces damage which may occur due to pressure or handling of the delicate lenses. Likewise, damage to the eye tissue during insertion of the instrument tips is reduced.

This invention may be further developed within the scope of the following claims. Accordingly, it is desired that the claims be read as illustrative of an operative embodiment of this invention and not in a strictly limiting sense.

I claim:

1. A surgical tool for use in folding and inserting an intraocular lens through a small incision into the anterior chamber of an eye, comprising:

an open channel formed with a base, spaced apart side walls and an open top, with the upper edges of the walls being spaced apart a distance corresponding to the width of an intraocular lens, so that an unfolded intraocular lens may be positioned in the channel, at a distance above the base of the channel, with the lens central axis substantially parallel to the axis of the channel;

an elongated, narrow pressing member associated with said channel and located above the channel open top in alignment with the axis of the channel and being movable towards and away from the channel base for engaging the lens along a narrow, central line located midway between and parallel to the channel walls and for pressing the center of the lens, along its central line, deeper into the channel towards the channel base to thereby fold the lens in half between the channel walls;

means for coupling said channel with said pressing member, a pair of opposed, laterally spaced apart, lens holding means releasably held within the channel, with each lens holding means adjacent a wall of the channel, so that the lens is folded between the lens holding means by the pressing member;

means for moving the lens holding means towards each other for gripping and squeezing the folded lens therebetween and for holding the lens in folded condition for removal from the channel and for inserting the lens into said eye chamber.

2. A surgical tool as defined in claim 1, and including said lens holding means being formed of elongated, resilient tips on the free ends of relatively movable forceps legs whose opposite ends are connected together so that the legs, and therefore the tips, can be moved towards and away from each other.

3. A surgical tool as defined in claim 2, and including at least one of said tips being formed of an elongated top of resilient wire bent into an elongated U-shape whose bent bight forms an insertion end portion and whose wire legs are generally parallel and have their free end portions arranged close together and connected to the adjacent forceps leg, with the wire leg intermediate portions that are located between the insertion end portion and the free end portions being spaced apart from each other a greater distance than the distance between the wires at the insertion end portion, wherein the insertion end portion forms an insertion guide for entering through an incision.

4. A surgical tool as defined in claim 3, and including each of said tips being similarly, but oppositely constructed and with the intermediate portions of each tip being bowed outwardly away from the intermediate portion of the other tip for gripping the lens along two, opposed pairs of generally parallel lines formed by the engagements between the tip wires and the lens.

5. A surgical tool as defined in claim 2, and including clips for releasably engaging the forceps legs for connecting the forceps and the channel together for folding the lens and for disconnecting the forceps from the channel after the lens is folded.

6. A surgical tool as defined in claim 1, and said pressing member being formed by a narrow, elongated end portion of an elongated member;

and with the channel base being secured upon an end portion of a second elongated member, and with the opposite ends of said elongated members being connected together to form a forceps-like assembly wherein the elongated members may be moved towards and away from each other for moving the pressing member into and out of the channel;

and the opposite end of the channel being open for passage of the pressing member into and out of the channel and for moving said forceps leg tips into and out of said channel.

7. A surgical forceps as defined in claim 6, and including the base of said channel having a base extension portion extending outwardly of the end of the channel which is remote from the connection between the elongated members; and clip means formed upon the base extension portion for engaging and releasably fastening said forceps legs to the channel.

8. A surgical tool for folding and inserting an intraocular lens through a small incision into the anterior chamber of an eye, comprising:

an open channel formed with a base, spaced apart side walls and an open top, with the upper edges of the walls being spaced apart a distance corresponding to the width of a lens so that an intraocular lens may be placed in the channel between the side walls and extend across the channel open top at a distance above the base of the channel, with the central axis of the lens in substantial parallel alignment with the axis of the channel;

said channel being mounted upon the end of one leg of a forceps with the opposite leg having an end portion forming an elongated pressing member located above the open top of the channel in alignment with the axis of the channel so that the pressing member may be moved towards the channel base, between the channel walls for pressing a lens, along the center line of the lens, into the channel for folding the lens in half between the channel walls;

an insertion forceps having elongated, resilient tips formed on the free ends of its legs;

said tips being releasably held within the channel, with each tip located adjacent a side wall of the channel and the base of the channel, with the tips spaced apart, so that the lens rests upon the tips, and the lens is folded by moving the pressing member towards the channel base between the lens holding tips;

said tips being movable towards each other for gripping the folded lens between the tips and for holding the lens in folded condition for removal from the channel and for inserting the lens into said chamber.

9. A surgical tool as defined in claim 8, and including releasable locking means for holding the insertion forceps legs in fixed relationship when the legs are moved towards each other for gripping a folded lens between the tips of the legs, with said locking means being manually releasable for separating the tips sufficiently to release the folded lens when the tips containing the folded lens is inserted within the chamber of the eye.

10. A surgical tool as defined in claim 9, and including clip means formed on the base of the channel for temporarily securing the insertion forceps legs to the channel with the tips located within the channel against their respective side walls.

11. A surgical tool as defined in claim 10, and including said tips each being formed of resilient wire bent into an elongated U-shaped forming a bent bight and a pair of substantially parallel wire legs, and with the free end portions of the legs permanently secured to their respective forceps legs;

whereby the resilient wire tips each press against one side of the folded lens along a substantially parallel pair of lines defined by the engagements between the wires and the lens for resiliently gripping and squeezing the lens.

12. A surgical tool as defined in claim 11, and wherein the wire portions adjacent the bights of the wire tips are more closely spaced from each other than the wire portions between them and the free end portions of the wire that are fastened to the respective forceps legs to form a narrower lead end on the tips at the bights of the U-shapes; and with the wire portions extending between the lead end portions and the free end portions that are fastened to the forceps being bowed outwardly relative to the opposing tip wires for gripping the lens between the bowed portions.

13. A surgical forcept for holding and for inserting a folded intraocular lens through a small incision in the limbus into the anterior chamber of an eye, comprising:

a pair of legs jointed together at one of their ends for movement of their opposite free ends towards and away from each other;

elongated, aligned tips formed on the opposite free ends of the legs;

said tips each being formed of a resilient wire bent into an elongated U-shape having a bight and a pair of generally parallel wire legs;

said wire legs being divided along their lengths into a bight end portion, an elongated intermediate portion, and a free end portion;

with the wire legs of the intermediate portions being spaced apart a predetermined distance, and the wire legs at the bight end portions being spaced apart a considerably lesser distance, and the wire legs at the free end portions being closely adjacent to each other and fixedly secured to their adjacent forceps leg;

whereby a folded lens may be located between the two opposing, aligned tip intermediate portions and will be substantially linearly engaged by the two pairs of spaced wires for resiliently squeezing and holding the folded lens until the forceps legs are moved apart for releasing the lens within said chamber so that the lens is inserted and unfolds within the chamber without damaging the lens.

14. A surgical forceps as defined in claim 13, and including each of said tip intermediate portions being outwardly bowed apart relative to the opposite tip intermediate portion; and with the bight portions and free end portions of the two tips being roughly parallel to each other.

15. A surgical forceps as defined in claim 14, and including latching means for releasably locking the forceps legs together, against outward movement, when the leg tips grip a folded lens between them, with said latching means being manually releasable for moving the forceps legs and their tips apart a distance sufficiently for releasing the folded lens from between the tips.

* * * * *

UNITED STATES PATENT AND TRADEMARK OFFICE
CERTIFICATE OF CORRECTION

PATENT NO. : 4,844,093
DATED : July 4, 1989
INVENTOR(S) : Robert S. Jampel, Dian X. Shi It is certified that error appears in the above-identified patent and that said Letters Patent is hereby corrected as shown below:

In claim 3, col. 6, line 4, change "top" to --loop--
In claim 6, col. 6, line 40, change "forcepts" to --forceps--
In claim 13, col. 8, line 4, change "forcept" to --forceps--
In claim 13, col. 8, line 7, change "jointed" to --joined--

Signed and Sealed this

Tenth Day of April, 1990

Attest:

HARRY F. MANBECK, JR.

*Attesting Officer*  *Commissioner of Patents and Trademarks*